United States Patent
Liakatos

(10) Patent No.: US 12,351,557 B2
(45) Date of Patent: Jul. 8, 2025

(54) CHEMICAL COMPOUND MANUFACTURE, NEW SALT FORM, AND THERAPEUTIC USES THEREOF

(71) Applicant: Eustralis Pharmaceuticals Limited (Trading As Pressura Neuro), Melbourne (AU)

(72) Inventor: Angela Liakatos, Boronia (AU)

(73) Assignee: Eustralis Pharmaceuticals Limited, Melbourne (AU)

(*) Notice: Subject to any disclaimer, the term of this patent is extended or adjusted under 35 U.S.C. 154(b) by 241 days.

(21) Appl. No.: 17/416,741

(22) PCT Filed: Dec. 24, 2019

(86) PCT No.: PCT/AU2019/051433
§ 371 (c)(1),
(2) Date: Jun. 21, 2021

(87) PCT Pub. No.: WO2020/132716
PCT Pub. Date: Jul. 2, 2020

(65) Prior Publication Data
US 2022/0073467 A1    Mar. 10, 2022

(30) Foreign Application Priority Data
Dec. 24, 2018   (AU) .............................. 2018904929

(51) Int. Cl.
*C07D 213/82*   (2006.01)
(52) U.S. Cl.
CPC .................... *C07D 213/82* (2013.01)
(58) Field of Classification Search
CPC .................................................. C07D 213/82
See application file for complete search history.

(56) References Cited

U.S. PATENT DOCUMENTS

| | | | |
|---|---|---|---|
| 2002/0091265 A1* | 7/2002 | Bos .................... | A61P 25/30 546/276.4 |
| 2003/0130511 A1* | 7/2003 | Lida .................... | C07D 213/84 548/215 |
| 2015/0218151 A1* | 8/2015 | Ogamino ............... | A61P 9/00 544/405 |
| 2018/0244668 A1* | 8/2018 | Platzek .................. | C25B 3/25 |

FOREIGN PATENT DOCUMENTS

| | | | |
|---|---|---|---|
| CN | 109384712 A | | 2/2019 |
| EP | 1035115 | * | 9/2000 |
| EP | 1394150 A1 | | 3/2004 |
| WO | 2019148246 A1 | | 8/2019 |
| WO | 2019148247 A1 | | 8/2019 |

OTHER PUBLICATIONS

Zala et al., Laboratory Techniques of Purification and Isolation, 2012, Int. J. Drug Dev. & Res, vol. 4, No. 2, p. 41-55 (Year: 2012).*
Hoffmann-Emery, F. , et al., "Efficient synthesis of novel NK1 receptor antagonists: selective 1,4-addition of grignard reagents to 6-chloronicotinic acid derivatives.", J Org Chem. Mar. 3, 2006;71(5):2000-8. doi: 10.1021/jo0523666. PMID: 16496986. (Abstract Only).
PCT International Search Report and Written Opinion in PCT/AU2019/051433 dated Mar. 19, 2020, 13 pages.
IDT Australia Limited, Summary Report REP1002, "Development of the GMP Manufacture of EU-C-001 HCL Salt", Oct. 8, 2018, 54 pages.
Sharma et al.; "The Importance of Good Manufacturing Practices (GMP) in the Healthcare Industry", J. Pharm. Res. Int., vol. 35, No. 18, pp. 75-90, 2023; Article No. JPRI. 101385.

* cited by examiner

*Primary Examiner* — Samantha L Shterengarts
*Assistant Examiner* — Karen Cheng
(74) *Attorney, Agent, or Firm* — SERVILLA WHITNEY LLC

(57) ABSTRACT

There is disclosed a method of preparing a compound of Formula (1), or a salt thereof (1) the method comprising: a) treating a compound of Formula (2) sequentially with o-tolylmagnesium chloride, N-methylpiperazine and iodine, under conditions sufficient to obtain a compound of Formula (3) b) treating the compound of Formula (3) from step a) with 3,5-bis(trifluoromethyl)benzyl bromide and a suitable base, under conditions sufficient to obtain a compound of Formula (1).

16 Claims, 8 Drawing Sheets

$^1$H-NMR – Compound (1) Free Base

| Chemical Shift (ppm) | Multiplicity | No. of Protons | Assignment |
|---|---|---|---|
| 2.10 | s | 3H | 17-$CH_3$ |
| 2.21 | s | 3H | 1-$NCH_3$ |
| 2.38 | m | 4H | 2-$CH_2$, 5-$CH_2$ |
| 2.69 | s | 3H | 19-$NCH_3$ |
| 3.56 | m | 4H | 3-$CH_2$, 4-$CH_2$ |
| 4.59 | m | 2H | 20-$CH_2$ |
| 6.64 | s | 1H | 10-CH |
| 7.01 | s | 1H | 12-CH, 13-CH |
| 7.13 | brs | 3H | 14-CH, 15-CH |
| 7.74 | s | 2H | 22-CH, 26-CH |
| 7.99 | s | 1H | 24-CH |
| 8.17 | s | 1H | 7-CH |
| Residual *tert*-Butyl Methyl Ether | | | |
| 1.21 | s | 9H | (C$H_3$)$_3$COCH$_3$ |
| 3.08 | s | 3H | (CH$_3$)$_3$COC$H_3$ |

$^{13}$C-NMR – Compound (1) Free Base

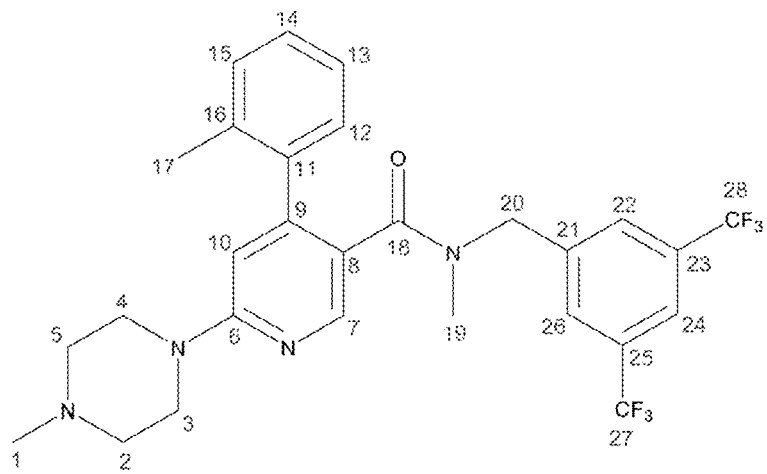

| Chemical Shift (ppm) | Multiplicity | No. of Carbons | Coupling Constant (Hz) | DEPT Assignment | Assignment |
|---|---|---|---|---|---|
| 19.67 | s | 1C | NIA | -CH or -CH$_3$ | 17-CH$_3$ |
| 36.58 | s | 1C | NIA | -CH or -CH$_3$ | 19-NCH$_3$ |
| 44.25 | s | 2C | NIA | -C or -CH$_2$ | 2-CH$_2$, 5-CH$_2$ |
| 45.74 | s | 1C | NIA | -CH or -CH$_3$ | 1-NCH3 |
| 48.97 | s | 1C | NIA | -C or -CH$_2$ | 20-CH$_2$ |
| 54.30 | s | 2C | NIA | -C or -CH$_2$ | 3-CH$_2$, 4-CH$_2$ |
| 107.11 | s | 1C | NIA | -CH or -CH$_3$ | 10-CH |
| 120.86 | s | 1C | NIA | -C or -CH$_2$ | 8-CH |
| 121.12 | s | 1C | NIA | -CH or -CH$_3$ | 24-CH |
| 123.22 | q | 2C | $^1J_{CF}$ 273 | -CH or -CH$_3$ | 27-CF3, 28-CF3 |
| 124.95 | s | 1C | NIA | -CH or -CH$_3$ | 12-CH/13-CH 14-CH/15-CH |
| 127.81 | s | 1C | NIA | | |
| 128.31 | s | 1C | NIA | | |
| 128.82 | s | 2C | NIA | -CH or -CH$_3$ | 22-CH, 26-CH |
| 128.74 | s | 1C | NIA | CH or -CH$_3$ | 12-CH/13-CH 14-CH/15-CH |
| 130.18 | q | 2C | $^2J_{CF}$ 33 | -C or -CH2 | 23-C, 25-C |
| 134.65 | s | 1C | NIA | -C or -CH2 | 11-C, 16-C, 21-C |
| 137.98 | s | 1C | NIA | | |
| 140.51 | s | 1C | NIA | | |
| 146.38 | s | 1C | NIA | -CH or -CH3 | 7-CH |
| 148.38 | s | 1C | NIA | -C or -CH2 | 6-C, 9-C |
| 158.65 | s | 1C | NIA | | |
| 168.82 | s | 1C | NIA | -C or -CH2 | 18-C=O |
| Residual *tert*-Butyl Methyl Ether | | | | | |
| 26.79 | s | 1C | NIA | -CH or -CH3 | (*CH3*)*3*COCH3 |
| 48.69 | s | 1C | NIA | -CH or -CH3 | (CH3)3CO*CH3* |

Figure 3

$^1$H-NMR – Compound (1) 2HCl Salt

| Chemical Shift (ppm) | Multiplicity | No. of Protons | Assignment |
|---|---|---|---|
| 2.14 | s | 3H | 17-CH$_3$ |
| 2.71 | s | 3H | 19-NCH$_3$ |
| 2.80 | s | 3H | 1-NCH$_3$ |
| 3.22 | m | 2H | 3-CH$_2$, 4-CH$_2$ |
| 3.50 | m | 2H | 2-CH$_2$/5-CH$_2$ |
| 3.61 | m | 2H | 3-CH$_2$/4-CH$_2$ |
| 4.59 | m | 4H | 2-CH$_2$/5-CH$_2$ 20-CH$_2$ |
| 6.98 | m | 1H | 10-CH |
| 7.03 | m | 1H | 12-CH, 13-CH |
| 7.13 | m | 3H | 14-CH, 15-CH |
| 7.72 | s | 2H | 22-CH, 26-CH |
| 7.91 | s | 1H | 24-CH |
| 8.25 | s | 1H | 7-CH |
| 11.89 | brs | 1H | NH$^+$Cl$^-$ |
| Residual *tert*-Butyl Methyl Ether | | | |
| 1.05 | s | 9H | (*CH$_3$*)$_3$COCH$_3$ |
| 3.03 | s | 3H | (CH$_3$)$_3$CO*CH$_3$* |

$^{13}$C-NMR – Compound (1) 2HCl Salt

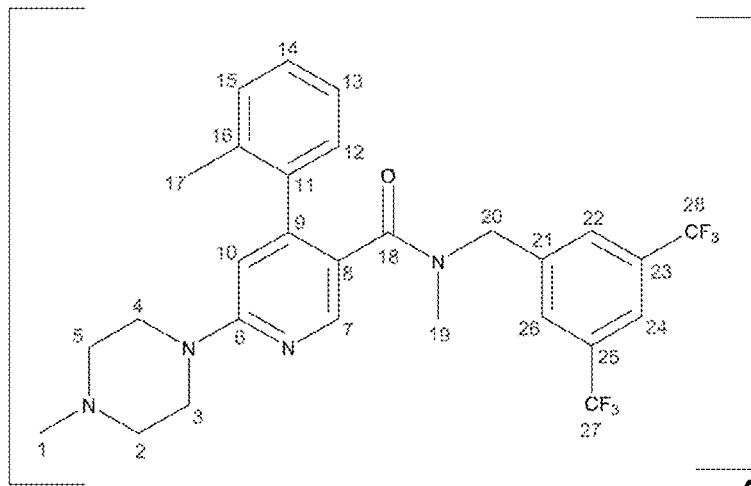

| Chemical Shift (ppm) | Multiplicity | No. of Carbons | Coupling Constant (Hz) | DEPT Assignment | Assignment |
|---|---|---|---|---|---|
| 19.67 | s | 1C | NIA | -CH or -CH3 | 17-CH3 |
| 36.59 | s | 1C | NIA | -CH or -CH3 | 19-NCH3 |
| 41.88 | s | 1C | NIA | -CH or -CH3 | 1-NCH3 |
| 43.00 | s | 2C | NIA | -C or -CH2 | 2-CH2, 5-CH2 |
| 49.18 | s | 1C | NIA | -C or -CH2 | 20-CH2 |
| 51.43 | s | 2C | NIA | -C or -CH2 | 3-CH2, 4-CH2 |
| 111.26 | s | 1C | NIA | -CH or -CH3 | 10-CH |
| 121.10 | s | 1C | NIA | -C or -CH2 | 8-C |
| 122.53 | s | 1C | NIA | -CH or -CH3 | 24-CH |
| 123.26 | q | 2C | $^1J_{CF}$ 263 | -CH or -CH3 | 27-CF3, 28-CF3 |
| 125.05 | s | 1C | NIA | -CH or -CH3 | 12-CH13-CH |
| 128.10 | s | 1C | NIA | | |
| 128.55 | s | 1C | NIA | | 14-CH15-CH |
| 129.07 | s | 2C | NIA | -CH or -CH3 | 22-CH, 26-CH |
| 129.99 | s | 1C | NIA | -CH or -CH3 | 12-CH13-CH 14-CH15-CH |
| 130.31 | q | 2C | $^2J_{CF}$ 33 | -C or -CH2 | 23-C, 25-C |
| 134.94 | s | 1C | NIA | | |
| 136.61 | s | 1C | NIA | -C or -CH2 | 11-C, 16-C, 21-C |
| 140.21 | s | 1C | NIA | | |
| 140.83 | s | 1C | NIA | -CH or -CH3 | 7-CH |
| 151.68 | s | 1C | NIA | -C or -CH2 | 6-C, 9-C |
| 154.38 | s | 1C | NIA | | |
| 166.98 | s | 1C | NIA | -C or -CH2 | 18-C=O |
| Residual *tert*-Butyl Methyl Ether | | | | | |
| 26.77 | s | 1C | NIA | -CH or -CH3 | (*CH3*)*3*COCH3 |
| 48.71 | s | 1C | NIA | -CH or -CH3 | (CH3)3CO*CH3* |

Figure 5

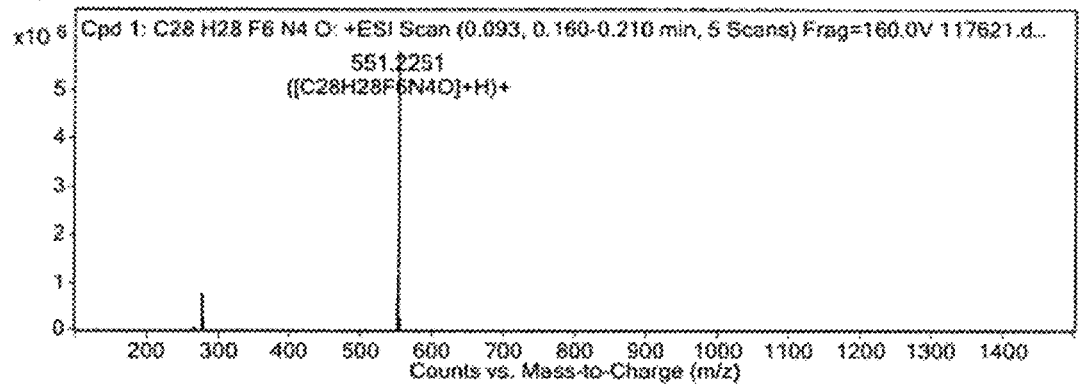
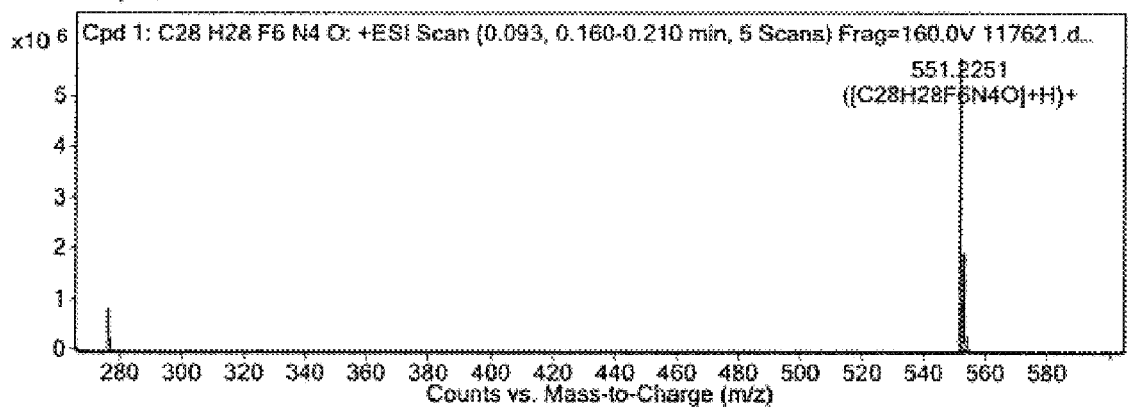
MS Spectrum Peak List
| m/z | Calc m/z | Diff(ppm) | z | Abund | Formula | Ion |
|---|---|---|---|---|---|---|
| 276.1162 | 276.1156 | -2.09 | 2 | 845804.91 | C28H28F6N4O | (M+2H)+2 |
| 551.2251 | 551.224 | -2.03 | 1 | 5848155.57 | C28H28F6N4O | (M+H)+ |
| 573.2055 | 573.206 | 0.84 | 1 | 4897.01 | C28H28F6N4O | (M+Na)+ |
Figure 6

CHEMICAL COMPOUND MANUFACTURE, NEW SALT FORM, AND THERAPEUTIC USES THEREOF

CROSS REFERENCE TO RELATED APPLICATIONS

This is a National Phase entry of International Application No. PCT/AU2019/051433, filed Dec. 24, 2019, which claims priority to Australian Patent Application No. AU 2018904929, filed Dec. 24, 2018, the disclosures of which are incorporated herein by reference in their entireties.

FIELD

The present invention relates to the synthesis of a particular substituted pyridine compound and/or a salt form, together with a new salt form, and therapeutic uses thereof.

BACKGROUND

U.S. Pat. No. 6,303,790 discloses, inter alia, the synthesis of substituted pyridine compounds of the following general formula:

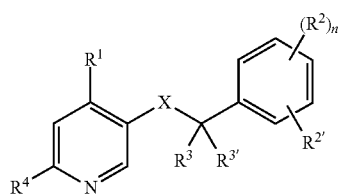

These compounds have shown antagonist activity at the neurokinin 1 (NK-1, substance P) receptor and may be useful for the treatment or prevention of certain central nervous system disorders. The synthetic route to these substituted pyridines includes the installation and removal of protecting groups and the introduction of reactive functional groups to the substrate for subsequent reactions. These additional steps reduce the overall efficiency and atom economy of the synthesis. Furthermore, purification procedures of the compounds and their intermediates often include chromatographic processes.

EP 1394150 discloses, inter alia, the synthesis of phenyl-substituted pyridine compounds of the following general formula:

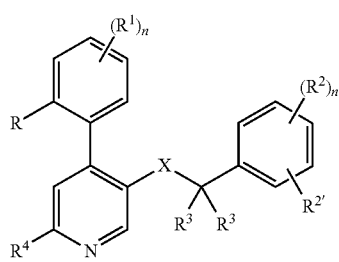

The synthetic route disclosed requires multiple steps including palladium-catalysed coupling of aryl boronic acids to install the phenyl substituent, reactions at very high (130° C.) or very low (−78° C.) temperatures and the use of protecting groups. The document also discloses that each intermediate is isolated by column chromatography, which is time- and resource-consuming. In general, the synthetic route disclosed teaches the synthesis of the target compound and its intermediates on a milligram or gram scale, with each intermediate (and hence the target compound) produced in moderate yields.

The routes of the prior art to these substituted pyridines typically employ a large number of synthetic steps and reaction conditions, which when considered alone or together, results in obstacles to the synthesis of these compounds on a larger scale.

Even while the obstacles of the method or route may be overcome, the form of the compound may be important or desirable for its manufacture into a product. The form of the compound may also be important or desirable for its utility as a product. For example, certain characteristics such as processability, flowability, heat stability, consistency, etc are desirable during the manufacturing process which may be only provided by certain forms of the compound. Further, certain characteristics of the product such as shelf-life, coloration, efficacy, release rate, etc are desirable and which may only be provided by certain forms of the compound. In this regard, when these characteristics are considered alone or together, certain forms of the compound may be more desirable than other forms of the compound.

The present invention is directed to providing a more efficient route to prepare particular substituted pyridine compounds in high amounts, large scale, and which is amenable to GMP processing. The present invention is also directed to particularly substituted pyridine compounds and/or particular salt forms thereof which demonstrate specific processing and therapeutic advantages, especially for the preparation of intravenous formulations.

SUMMARY OF THE INVENTION

In one aspect, the present invention provides a method of preparing a compound of Formula (1), or a salt thereof:

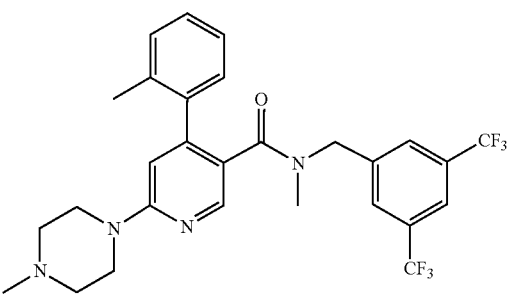

the method comprising:
a) treating a compound of Formula (2):

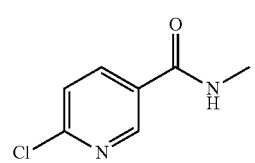

sequentially with o-tolylmagnesium chloride, N-methylpiperazine and iodine, under conditions sufficient to obtain a compound of Formula (3):

b) treating the compound of Formula (3) from step a) with 3,5-bis(trifluoromethyl)benzyl bromide and a suitable base, under conditions sufficient to obtain a compound of Formula (1).

The term "sequentially" as used herein and when used in relation to a series of reagents, refers to the successive addition of the listed reagents to the substrate in a manner that allows the intended reaction of the added reagent to occur before the addition of the next listed reagent, and where the products of the reaction are not isolated until after the final reagent listed is added to the reaction.

In another aspect, the present invention provides a method for preparing a dihydrochloride salt of the compound of Formula (1):

a) treating a compound of Formula (2):

sequentially with o-tolylmagnesium chloride, N-methylpiperazine and iodine, under conditions sufficient to obtain a compound of Formula (3):

b) treating the compound of Formula (3) from step a) with 3,5-bis(trifluoromethyl)benzyl bromide and a suitable base, under conditions sufficient to obtain a compound of Formula (1); and c) treating the compound of Formula (1) obtained from step b) with a solution of hydrochloric acid in diethyl ether, under conditions sufficient to obtain a dihydrochloride salt of the compound of Formula (1).

In still another aspect, the present invention provides a compound of Formula (1) or a salt thereof:

produced according to an aforementioned aspect.

In yet another aspect, the present invention provides a dihydrochloride salt of the compound of Formula (1):

BRIEF DESCRIPTION OF THE FIGURES

FIG. 3—$^{13}$C NMR Data of Compound (1) Free Base (150 MHz, DMSO-d6) (20.5 mg) (Relative to DMSO-$d^6$ at 39.57 ppm).

FIG. 4—1H-NMR Spectrum of Compound (1) 2HCl Salt (600 MHz, DMSO-d6) (200 mg) (Relative to DMSO-d6 at 2.50 ppm).

FIG. 5—$^{13}$C NMR Data of Compound (1) Salt (150 MHz, DMSO-d6) (200 mg) (Relative to DMSO-d6 at 39.57 ppm).

FIG. 6—Mass Spectrum of Compound (1) 2HCl salt.

DETAILED DESCRIPTION OF THE INVENTION

Figure 1:
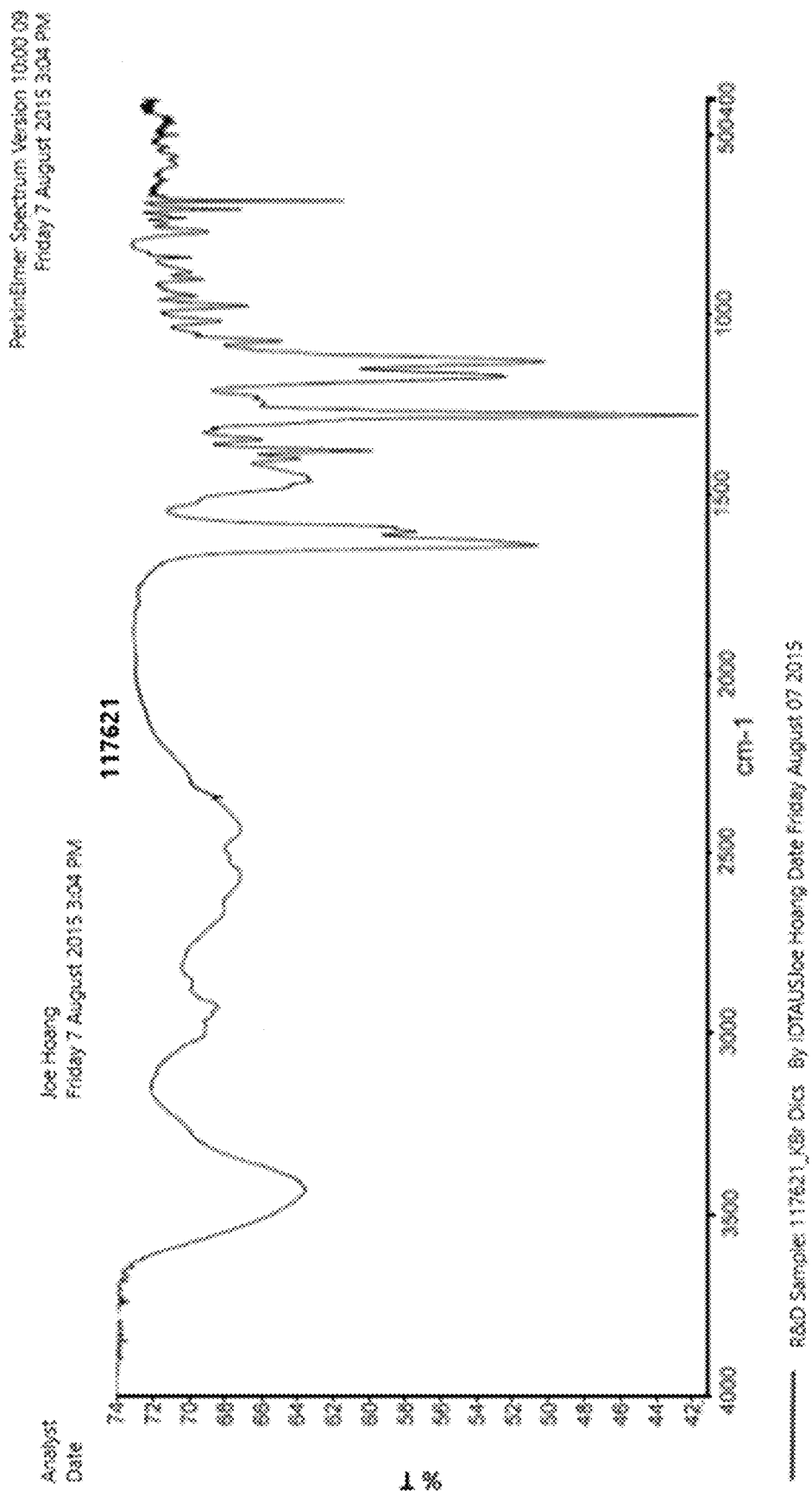
FIG. 1—FT-IR Spectrum of Compound (1) 2HCl salt.

Throughout this specification and the claims that follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention is based on the unexpected discovery that the compound of Formula (1) and/or salts thereof can be prepared efficiently in kilogram-scale quantities, in good to high yields. The processes disclosed herein are shown to be amenable to scale-up and allows production of compounds of Formula (1) and/or salts thereof on a large scale in an efficient and safe manner amenable to GMP conditions for the production of material suitable for medical administration. The efficiency of the processes is improved by employing steps that minimise the use of protecting groups on reagents and substrates and can be performed without the use of very high or very low temperatures, as shown in the appended examples.

The present inventors have found that a compound of Formula (3)

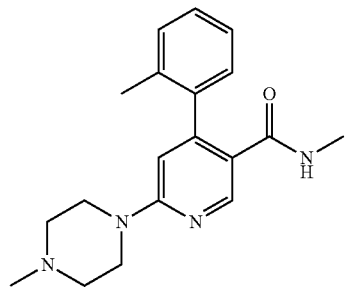

(3)

can be obtained by sequentially treating a compound of Formula (2)

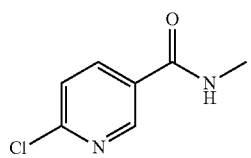

(2)

with o-tolylmagnesium chloride, N-methylpiperazine and iodine. The present inventors have also found that the intermediates obtained from the treatment of the compound of Formula (2) with o-tolylmagnesium chloride and N-methylpiperazine do not require isolation prior to subsequent steps of the reaction, and that simple purification procedures to remove reaction impurities may provide a compound or intermediate of sufficient purity for the subsequent reaction.

As used herein, the term "isolated" when referring to a compound or intermediate refers to the compound or intermediate being physically removed from any other compound, solvent or substance. As used herein, the reference to a "purification" step is distinct from an "isolation" step, with only completion of the latter providing a compound or intermediate in an isolated form, and completion of the former providing a compound or intermediate in the presence of at least one other compound, solvent or other substance. For instance a purification step may involve steps such as washing with an aqueous or organic solvent, acid-base extraction, simple filtration or solvent swaps. This is to be contrasted with chromatographic separation steps, for example, flash column chromatography, liquid chromatography and other preparative chromatography methods, which provide the compound in a substantially pure form.

Thus in certain embodiments, the processes of the present invention are performed on a multi-gram scale. In certain embodiments, the processes of the present invention are performed on a kilogram scale. In certain embodiments, the processes of the present invention are performed on a multi-kilogram scale.

In an embodiment, the method comprises treating an amide of Formula (2) with o-tolylmagnesium chloride under conditions to produce an intermediate of Formula (5a), which may tautomerise in situ to a compound of Formula (5b):

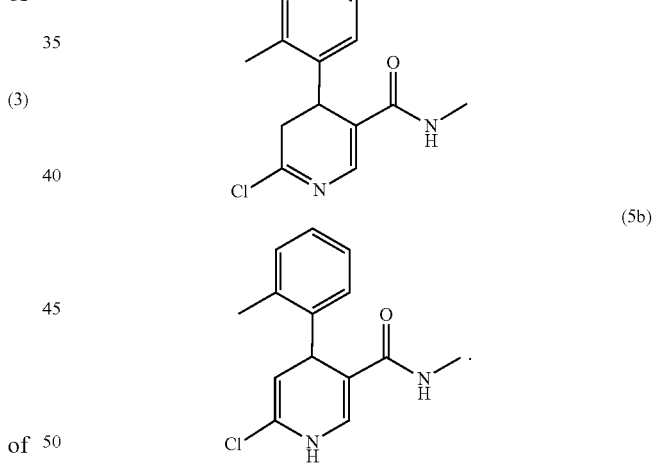

In certain embodiments, the reaction between the amide of Formula (2) and o-tolylmagnesium chloride may be performed in tetrahydrofuran (THF). In certain embodiments, the THF is anhydrous. In certain embodiments, the reaction is performed at a temperature range of −5° C. to 5° C., such as about −5° C., −4° C., −3° C., −2° C., −1° C., 0° C., 1° C., 2° C., 3° C., 4° C. or 5° C. In an embodiment, the reaction between the amide of Formula (2) and o-tolylmagnesium chloride is performed at a temperature of about 0° C. In an embodiment, the reaction between the amide of Formula (2) and o-tolylmagnesium chloride is performed in anhydrous THF at a temperature of about 0° C.

In certain embodiments, the reaction between the amide of Formula (2) and o-tolylmagnesium chloride is performed by adding the amide of Formula (2) to a solution of o-tolylmagnesium chloride. In certain embodiments, the solution of o-tolylmagnesium chloride is a solution in THF. In certain embodiments, the solution of o-tolylmagnesium chloride is a solution in THF with a concentration of 1 mol/L. In certain embodiments, the amide of Formula (2) is added dropwise to the solution of o-tolylmagnesium chloride. In certain embodiments, the amide of Formula (2) is added dropwise to the solution of the o-tolylmagnesium chloride at a temperature of about 0° C. In certain embodiments, the amide of Formula (2) is added dropwise to the solution of the o-tolylmagnesium chloride at a temperature of about 0° C. over a time of about 1 hour. In certain embodiments, the reaction between the amide of Formula (2) and o-tolylmagnesium chloride is stirred for at least 1 hour. In certain embodiments, the reaction between the amide of Formula (2) and o-tolylmagnesium chloride is stirred for at least 1 hour at a temperature of about 20° C.

The reaction between the amide of Formula (2) and o-tolylmagnesium chloride may be monitored by high-performance liquid chromatography (HPLC). In certain embodiments, the reaction between the amide of Formula (2) and o-tolylmagnesium chloride is stirred at a temperature of about 20° C., until HPLC analysis shows that the amide of Formula (2) is present in an amount of no more than about 8% of the reaction mixture. In certain embodiments, where HPLC analysis of the reaction between the amide of Formula (2) and o-tolylmagnesium chloride indicates that the amide of Formula (2) is present in an amount greater than about 8%, a further aliquot of o-tolylmagnesium chloride as a solution in THF is added dropwise to the reaction mixture.

In certain embodiments, the reaction between the amide of Formula (2) and o-tolylmagnesium chloride is diluted with ethyl acetate when HPLC analysis shows that the amide of Formula (2) is present in an amount of no more than about 8% of the reaction mixture. In certain embodiments, the reaction between the amide of Formula (2) and o-tolylmagnesium chloride produces the compound of Formula (5a) and its tautomer Formula (5b). Given the tautomeric relationship between compounds of Formula (5a) and Formula (5b), any reference to the compound of Formula (5a) will be taken to mean the compound of Formula (5a) and its tautomer Formula (5b), where present, unless otherwise stated.

As it will be appreciated, the compound of Formula (5a) and its tautomer Formula (5b), where present, are not isolated from the reaction mixture in which they are formed and are subjected directly to a subsequent reaction.

The compound of Formula (5a) is then subjected to a reaction with N-methylpiperazine under conditions to produce a compound of Formula (4):

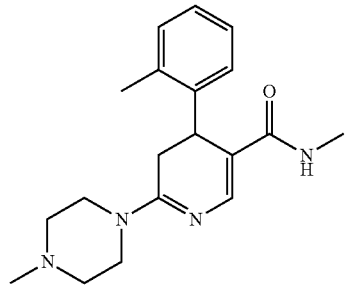

(4)

In certain embodiments, the N-methylpiperazine is added to the solution of Formula (5a). In certain embodiments, the compound of Formula (5a) is treated with about 5 molar equivalents of N-methylpiperazine. In certain embodiments, the reaction mixture of the compound of Formula (5a) and N-methylpiperazine is stirred at a temperature range of about 15° C. to 25° C., such as about 15° C., 16° C., 17° C., 18° C., 19° C., 20° C., 21° C., 22° C., 23° C., 24° C. or 25° C. In an embodiment, the reaction of the compound of Formula (5a) and N-methylpiperazine is stirred at a temperature of about 20° C. In certain embodiments, the reaction of the compound of Formula (5a) and N-methylpiperazine is stirred at about 20° C. for about 10 hours. In certain embodiments, the reaction between the compound of Formula (5a) and N-methylpiperazine is monitored by HPLC. In certain embodiments, the reaction between the compound of Formula (5a) and N-methylpiperazine is stirred at a temperature of about 20° C., until HPLC analysis shows that the compound of Formula (5a) (excluding its tautomer Formula (5b)) is present in an amount of no more than about 2% of the reaction mixture. In certain embodiments, the reaction between the compound of Formula (5a) and N-methylpiperazine produces a compound of Formula (4) in solution.

In certain embodiments, the reaction mixture comprising a compound of Formula (4) formed between the compound of Formula (5a) and N-methylpiperazine is cooled to a temperature range of about −5° C. to 5° C. when HPLC analysis shows that the compound of Formula (5a) is present in an amount of no more than about 2% of the reaction mixture. In certain embodiments, the temperature is about −5° C., −4° C., −3° C., −2° C., −1° C., 0° C., 1° C., 2° C., 3° C., 4° C. or 5° C. In certain embodiments, the reaction mixture comprising a compound of Formula (4) is diluted with an aqueous solution of acetic acid. In certain embodiments, the aqueous solution of acetic acid has a concentration of about 7%. In certain embodiments, the aqueous solution of acetic acid is added to the solution of Formula (4), such that the temperature of the resulting solution is no higher than about 20° C. In certain embodiments, the solution of Formula (4) has a pH of about 8 after the addition of the solution of acetic acid.

The compound of Formula (4) is not chromatographically isolated prior to any further reaction, yet may be subjected to purification prior to any further reaction. In certain embodiments, the compound of Formula (4) is purified by partitioning between an aqueous solution and an organic solvent. In certain embodiments, the compound of Formula (4) is purified by extraction into an organic phase from the aqueous phase. In certain embodiments, the aqueous solution is the solution in which the compound of Formula (4) is dissolved and may include the added acetic acid solution. In certain embodiments, the organic solvent is dichloromethane. In certain embodiments, the compound of Formula (4) is purified by extraction into dichloromethane from the aqueous phase. In certain embodiments, the compound of Formula (4) is purified by multiple extractions of the aqueous phase with dichloromethane. In certain embodiments, the aqueous phase is extracted with dichloromethane at least 2, 3 or 4 times. In certain embodiments, the extracts of dichloromethane containing the compound of Formula (4) are combined, dried with a drying agent and concentrated. In certain embodiments, the drying agent is anhydrous sodium sulfate. In certain embodiments, the compound of Formula (4) in dichloromethane is purified by a solvent swap. In certain embodiments, the compound of Formula (4) in dichloromethane is purified by a solvent swap with THF. In certain embodiments, the dichloromethane solution of a compound of Formula (4) is converted into a solution in THF by the addition of aliquots of THF and subsequent concentration of the solution under vacuum, until dichloromethane is removed and only THF remains as the solvent. It will be appreciated that the compound of Formula (4) is not isolated prior to any subsequent reaction.

The compound of Formula (4) is then subjected to a reaction with iodine under conditions to produce a compound of Formula (3):

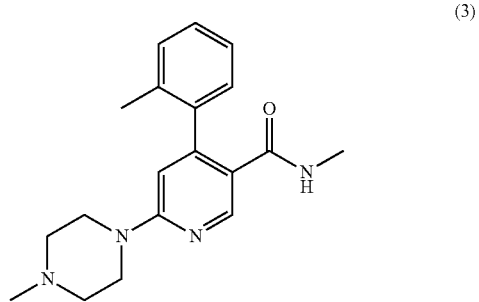

(3)

In certain embodiments, the compound of Formula (4) in a solution of THF is subjected to a reaction with iodine to produce a compound of Formula (3). In certain embodiments, the solution of Formula (4) in THF is cooled to a temperature in the range of about −5° C. to about 5° C., such as −5° C., −4° C., −3° C., −2° C., −1° C., 0° C., 1° C., 2° C., 3° C., 4° C. or 5° C., prior to a reaction with iodine. In certain embodiments, the iodine is in a solution of THF. In certain embodiments, the solution of iodine in THF is cooled to a temperature in the range of about −5° C. to about 5° C., such as −5° C., −4° C., −3° C., −2° C., −1° C., 0° C., 1° C., 2° C., 3° C., 4° C. or 5° C., prior to a reaction with the compound of Formula (4). In certain embodiments, a cooled solution of iodine is added to a cooled solution of a compound of Formula (4). In certain embodiments, the cooled solution of iodine is added in a dropwise manner to the cooled solution of a compound of Formula (4).

In certain embodiments, the reaction mixture of a compound of Formula (4) and iodine in THF is warmed to a temperature in the range of about 15° C. to about 25° C., such as 15° C., 16° C., 17° C., 18° C., 19° C., 20° C., 21° C., 22° C., 23° C., 24° C. or 25° C. In an embodiment, the reaction mixture is warmed to about 20° C. In certain embodiments, the reaction mixture of a compound of Formula (4) and iodine is stirred at a temperature of about 20° C. for about 15 h.

In certain embodiments, the reaction of a compound of Formula (4) and iodine is monitored by HPLC. In certain embodiments, the reaction of a compound of Formula (4) and iodine is stirred until HPLC analysis shows that the reaction comprises no more than 2% of the compound of Formula (4) present. In certain embodiments, stirring of the reaction of a compound of Formula (4) and iodine for more than 15 hours will result in a reaction mixture that contains more than 2% of the compound of Formula (4), according to HPLC analysis. Where more than 2% of the compound of Formula (4) is present after 15 hours, the reaction mixture is cooled to a temperature in the range of about −5° C. to about 5° C., such as −5° C., −4° C., −3° C., −2° C., −1° C., 0° C., 1° C., 2° C., 3° C., 4° C. or 5° C., and magnesium hydroxide and an aqueous solution of acetic acid added to the reaction mixture. In certain embodiments, 0.2 molar equivalents of magnesium hydroxide is added. In certain embodiments, the acetic acid is present in a concentration of about 10% v/v in the aqueous solution. In certain embodiments, the reaction mixture comprising a compound of Formula (4), iodine, magnesium hydroxide and acetic acid is warmed to a temperature in the range of about 15° C. to about 25° C., such as 15° C., 16° C., 17° C., 18° C., 19° C., 20° C., 21° C., 22° C., 23° C., 24° C. or 25° C., and stirred for at least 15 hours. In certain embodiments, the reaction mixture contains no more than 2% of the compound of Formula (4) according to HPLC analysis. In certain embodiments, the reaction mixture contains the compound of Formula (3).

In certain embodiments, the compound of Formula (3) is in a solution of THF, which further comprises iodine, magnesium hydroxide and acetic acid. In certain embodiments, the compound of Formula (3) is purified prior to the next reaction step. In certain embodiments, purification of the compound of Formula (3) requires cooling of the reaction mixture to a temperature in the range of about 0° C. to about 10° C., such as 0° C., 1° C., 2° C., 3° C., 4° C., 5° C., 6° C., 7° C., 8° C., 9° C. or 10° C., before an aqueous solution of sodium thiosulfate ($Na_2S_2O_3$) is added. In certain embodiments, the concentration of the aqueous solution of sodium thiosulfate is about 10%. In certain embodiments, the reaction mixture is maintained at a temperature of not more than 10° C. during the addition of the aqueous solution of sodium thiosulfate.

In certain embodiments, the compound of Formula (3) in a solution of THF and aqueous sodium thiosulfate is subjected to vacuum distillation, such that the THF present is removed. In certain embodiments, the vacuum distillation of THF from the reaction mixture containing the compound of Formula (3) is performed at a temperature of not more than 40° C.

In certain embodiments, the solution containing the compound of Formula (3) is cooled to a temperature in the range of about 0° C. to about 10° C., such as 0° C., 1° C., 2° C., 3° C., 4° C., 5° C., 6° C., 7° C., 8° C., 9° C. or 10° C., before an aqueous solution of hydrochloric acid is added.

In certain embodiments, the concentration of the aqueous solution of hydrochloric acid is about 2 mol/L. In certain embodiments, the solution containing the compound of Formula (3) is adjusted to a pH of between about 1 and about 2, as a result of the addition of the aqueous solution of hydrochloric acid. In certain embodiments, the solution containing the compound of Formula (3) is maintained at a temperature of not more than 10° C. during the addition of the aqueous solution of hydrochloric acid. In certain embodiments, the acidified aqueous solution is purified by extraction into ethyl acetate (EtOAc).

In certain embodiments, the acidified aqueous solution containing the compound of Formula (3) is adjusted to a pH of between about 8 and about 9, after extraction into ethyl acetate. In certain embodiments, an aqueous solution of sodium hydroxide (NaOH) is used to adjust the pH of the solution of Formula (3). In certain embodiments, the aqueous solution of NaOH has a concentration of about 2 mol/L. In certain embodiments, the solution containing a compound of Formula (3) is maintained at a temperature of not more than 10° C., during the addition of the aqueous solution of NaOH.

In certain embodiments, the solution of Formula (3) at a pH of between about 8 and about 9 is purified by phase extraction. In certain embodiments, the aqueous solution of Formula (3) is extracted into dichloromethane and the combined extracts of dichloromethane are dried with sodium sulfate ($Na_2SO_4$). In certain embodiments, the volume of the solution containing the compound of Formula (3) is reduced under vacuum. In certain embodiments, the solution of Formula (3) is at a concentration of about 20 mL/g compound.

The present inventors have found that the intermediate compound of Formula (3) does not require isolation in order for subsequent reactions to be performed, and can be purified sufficiently by solvent swap procedures.

In certain embodiments, the dichloromethane solution of the compound of Formula (3) is cooled to a temperature in the range of about 15° C. to about 25° C., such as 15° C., 16° C., 17° C., 18° C., 19° C., 20° C., 21° C., 22° C., 23° C., 24° C. or 25° C., and is then subjected to a solvent swap with methyl tert-butyl ether (MTBE). In certain embodiments, MTBE is added to the cooled solution of Formula (3). In certain embodiments, MTBE added to the cooled solution of Formula (3) over a time of about 20 minutes, about 30 minutes or about 40 minutes. In certain embodiments, the volume of the solution of Formula (3) in dichloromethane and MTBE is reduced under vacuum at a temperature of not more than 40° C. In certain embodiments, the solvent swap procedure with MTBE is repeated until the solution of Formula (3) contains dichloromethane at a concentration of no more than 3%, when analysed by gas chromatography. In certain embodiments, the solvent swap procedure is repeated at least twice.

In certain embodiments, the suspension of the compound of Formula (3) in MTBE is granulated for at least 1 hour at a temperature in the range of about 15° C. to about 25° C., such as 15° C., 16° C., 17° C., 18° C., 19° C., 20° C., 21° C., 22° C., 23° C., 24° C. or 25° C. In certain embodiments, the granulated compound of Formula (3) is isolated by filtration. In certain embodiments, the compound of Formula (3) is washed with an aliquot of MTBE. In certain embodiments, the compound of Formula (3) is washed with at least 5 aliquots of MTBE. In certain embodiments, the washed compound of Formula (3) is dried under vacuum at a temperature in the range of about 30° C. to about 40° C., such as 30° C., 31° C., 32° C., 33° C., 34° C., 35° C., 36° C., 37° C., 38° C., 39° C. or 40° C. In certain embodiments, the isolated compound of Formula (3) is a solid. In certain embodiments, the isolated compound of Formula (3) is an off-white solid. In certain embodiments, the isolated compound of Formula (3) is a brown solid. In certain embodiments, the isolated compound of Formula (3) is an off-white to brown solid. In certain embodiments, the compound of Formula (3) may be subjected to further isolation steps.

The compound of Formula (3) is then subjected to a reaction with 3,5-bis(trifluoromethyl)benzyl bromide and a base to produce a compound of Formula (1):

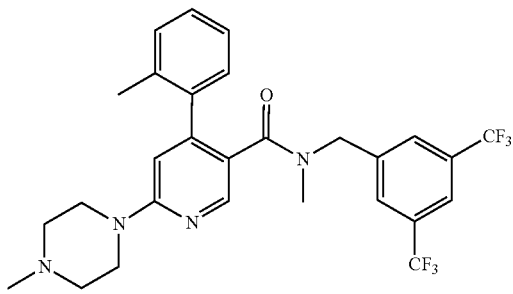

(1)

In certain embodiments, the base used is potassium tert-butoxide (KOtBu).

In certain embodiments, the isolated compound of Formula (3) is dissolved in THF. In certain embodiments, the THF is anhydrous. In certain embodiments, the compound of Formula (3) is dissolved in THF under an inert atmosphere. In certain embodiments, the inert atmosphere is an atmosphere of nitrogen. In certain embodiments, the isolated compound of Formula (3) is dissolved in THF under nitrogen at a temperature in the range of about −2.5° C. to about 7.5° C., such as −2.5° C., −1.5° C., −1° C., 0° C., 0.5° C., 1.5° C., 2.5° C., 3.5° C., 4.5° C., 5° C., 5.5° C., 6.5° C. or 7.5° C.

In certain embodiments, KOtBu is added to the compound of Formula (3) dissolved in THF. In certain embodiments, the mixture of KOtBu and the compound of Formula (3) is stirred for at least 15 minutes.

In certain embodiments, 3,5-bis(trifluoromethyl)benzyl bromide is added to the solution of KOtBu and compound of Formula (3). In certain embodiments, 3,5-bis(trifluoromethyl)benzyl bromide is added dropwise over a time of at least 30 minutes and at a temperature of not more than 5° C. In certain embodiments, the mixture of 3,5-bis(trifluoromethyl)benzyl bromide, KOtBu and compound of Formula (3) is stirred for at least 30 minutes at a temperature of not more than 5° C. In certain embodiments, the reaction of Formula (3) is stirred until analysis by HPLC shows that the compound of Formula (3) is present at a concentration of no more than 2%.

In certain embodiments, the reaction mixture containing no more than 2% of Formula (3) is diluted with water. In certain embodiments, the reaction mixture is at a temperature of no more than 20° C. when diluted with water. In certain embodiments, the diluted reaction mixture is acidified to a pH between about 1 and about 2. In certain embodiments, the diluted reaction mixture is acidified using an aqueous solution of hydrochloric acid. In certain embodiments, the aqueous solution of hydrochloric acid has a concentration of about 2 mol/L. In certain embodiments, the acidified reaction mixture is washed with n-heptane.

In certain embodiments, the acidified reaction mixture is adjusted to a pH of between about 8 and about 9. In certain embodiments, an aqueous solution of NaOH used to adjust the pH of the acidified reaction mixture. In certain embodiments, the aqueous solution of NaOH has a concentration of about 2 mol/L. In certain embodiments, the acidified reaction mixture is maintained at a temperature of not more than about 20° C. when the pH is adjusted with an aqueous solution of NaOH. In certain embodiments, the pH-adjusted reaction mixture is extracted into dichloromethane. In certain embodiments, the reaction mixture is extracted into dichloromethane at least 3 times. In certain embodiments, the combined extracts of dichloromethane are dried with sodium sulfate. In certain embodiments, the dried extracts of dichloromethane are circulated through a plug of silica gel. In certain embodiments, the dried extracts of dichloromethane are filtered through a plug of silica gel at least 3 times. In certain embodiments, the plug of silica gel is washed with dichloromethane. In certain embodiments, the silica gel is silica gel 60.

While compound of Formula (1) is very soluble or soluble in many solvents, the inventors have found that compound of Formula (1) is difficult to handle on a large scale. Without wanting to be bound by theory, the inventors believe that this may be due to compound of Formula (1) being amorphous and has a hydrophobic character. There was also no tendency of the compound of Formula (1) as its free base to form crystalline materials and shows no clear thermal events and no diffraction peaks. This is not desirable as the process time may be increased, which may be compounded by a greater loss of material when processing.

In this regard, to further explore the possibility of improving the handling of the compound in the manufacturing process and properties of the end product, an analysis of the interaction of compound of Formula (1) with various counterions and in various solvents was undertaken.

The skilled person would understand that such an undertaking is not straightforward and not obvious as many factors would need to be considered in order to justify its combination as a viable trial option. Further, there is a need to limit the number of combinations so that the analysis would be manageable. For example, physical properties of the compound such as pKa, pH, molecular mass, melting point, density, solubility, polarity, and appearance, and chemical properties such as degradation profile, reactivity, stability, and isomerism would need to be considered, not only for handling during the method process, but also to ensure that the compound remains active when formed as a product. Further, the salt form would also need to be analysed for its pharmacokinetic properties. Even while a certain salt form may provide desirable qualities in one aspect, for example the manufacturing process, its selection must still be assessed in view of its other qualities (e.g. pharmacokinetic properties). In this regard, to further complicate matters the compound of Formula (1) has 3 possible acidic sites. As such, improving and predicting critical physico-chemical properties of the formula (1) by salt formation is not straightforward.

The inventors have found that particular dihydrochloride salt form of compound of Formula (1) shows desirable properties especially for intravenous (IV) formulations. The aim was to consider where one could improve upon some of the critical physico-chemical properties of the compound of formula (1) (eg solubility, stability, bioavailability, etc). In this regard the inventors initially screened based on criteria such as crystallinity, polymorphic behaviour, solubility (especially for use in potential aqueous IV formulations). For example, the inventors found that formate, acetate, phosphate and sulfate salts have no tendency to form crystalline materials in any solvent used and were discounted on this basis. While citrate, tartarate, hydrobromate and methanesulfonate salts produce the best crystalline form which were initially thought could make them suitable candidates, some of these salt forms do not appear to be stable and show some degradation and/or polymorphism overtime. Such salts are also unstable at the usable pH and transform into an amorphous gel. Further, some of these salt forms start to decompose during melting, suggesting that processing these salts would be challenging.

With regard to the hydrochloride salt formation of a compound of Formula (1) the inventors postulated that the compound of Formula (1) could, in theory, form three salt forms: monohydrochloride, dihydrochloride and trihydrochloride. When the studies were actually performed it was found that the monohydrochloride salt still produces a sticky solid which is difficult to process and showed a relatively low tendency to form crystalline material. In comparison, the trihydrochloride salt is easier to process but is hygroscopic and requires a more lengthy and expensive process, which is not desirable. Also, the trihydrochloride slat form is more acidic than either the mono- or di-salt forms which would lead to local irritation if administered to a subject. In contrast, the dihydrochloride salt was surprisingly found to be ideal in terms of manageable processing, stability and therapeutic outcomes even though it is produced in an amorphous form. In certain embodiments the dihydrochloride is produced substantially free of either the mono or tri-hydrochloride, for eg, in greater than 95% purity.

Accordingly, in an embodiment, the present invention also provides a method of preparing a dihydrochloride salt of the compound of Formula (1):

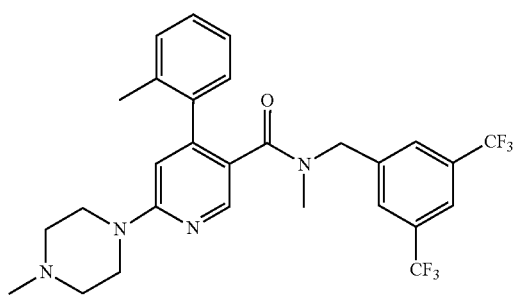

(1)

the method comprising:
a) treating a compound of Formula (2):

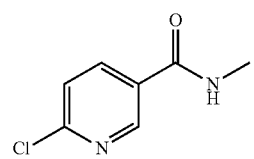

(2)

sequentially with o-tolylmagnesium chloride, N-methylpiperazine and iodine, under conditions sufficient to obtain a compound of Formula (3):

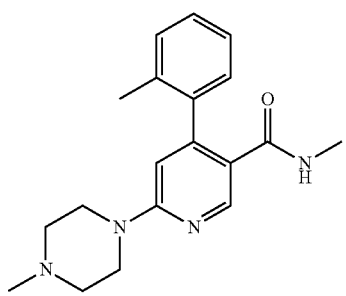

(3)

b) treating the compound of Formula (3) from step a) with 3,5-bis(trifluoromethyl)benzyl bromide and a suitable base, under conditions sufficient to obtain a compound of Formula (1);
c) treating the compound of Formula (1) with a solution of hydrochloric acid in diethyl ether, under conditions sufficient to obtain a dihydrochloride salt of the compound of Formula (1).

The present inventors have found that the compound of Formula (1) can be converted to a dihydrochloride salt. Furthermore, the present inventors have found that the compound of Formula (1) can be converted to a dihydrochloride salt without isolation of the free base of Formula (1), however in some embodiments, the compound of Formula (1) may be isolated before conversion to a dihydrochloride salt.

In certain embodiments, the combined extracts of dichloromethane containing the compound of Formula (1) obtained from filtration through silica gel are concentrated under vacuum at a temperature of not more than 40° C. In certain embodiments, the extracts of dichloromethane are concentrated to give the compound of Formula (1) in a solution of dichloromethane, where the solution has a concentration of about 10 mL/g of Formula (1). In certain embodiments, the solution of Formula (1) in dichloromethane is cooled to a temperature in the range of about −5° C. to about 5° C., such as −5° C., −4° C., −3° C., −2° C., −1° C., 0° C., 1° C., 2° C., 3° C., 4° C. or 5° C. In certain embodiments, an aqueous solution of hydrochloric acid is added to the cooled solution of Formula (1). In certain embodiments, the aqueous solution of hydrochloric acid is added dropwise to the cooled solution of Formula (1). In certain embodiments, the cooled solution of Formula (1) is maintained at a temperature in the range of about −5° C. to about 5° C., such as −5° C., −4° C., −3° C., −2° C., −1° C., 0° C., 1° C., 2° C., 3° C., 4° C. or 5° C., during the addition of the aqueous solution of hydrochloric acid. In certain embodiments, the concentration of the aqueous solution of hydrochloric acid is about 2 mol/L.

In certain embodiments, a suspension of a dihydrochloride salt of Formula (1) is obtained after the addition of hydrochloric acid. In certain embodiments, the suspension of the dihydrochloride salt of Formula (1) is stirred at a temperature in the range of about −5° C. to about 5° C., such as −5° C., −4° C., −3° C., −2° C., −1° C., 0° C., 1° C., 2° C., 3° C., 4° C. or 5° C., for about 1 h. In certain embodiments, MTBE is added to the suspension of the dihydrochloride salt of Formula (1) at a temperature of about 15° C. to about 25° C., such as 15° C., 16° C., 17° C., 18° C., 19° C., 20° C., 21° C., 22° C., 23° C., 24° C. or 25° C. In certain embodiments, MTBE added to the suspension of the dihydrochloride salt of Formula (1) over a time of about 20 minutes, about 30 minutes or about 40 minutes. In certain embodiments, the volume of the solution of Formula (1) suspended in dichloromethane and MTBE is reduced under vacuum at a temperature of not more than 40° C. In certain embodiments, the solvent swap procedure with MTBE is repeated until the solution of Formula (1) contains dichloromethane at a concentration of no more than 3%, when analysed by gas chromatography. In certain embodiments, the solvent swap procedure is repeated at least twice.

In certain embodiments, the suspension containing the dihydrochloride salt of Formula (1) is granulated at a temperature of about 15° C. to about 25° C., such as 15° C., 16° C., 17° C., 18° C., 19° C., 20° C., 21° C., 22° C., 23° C., 24° C. or 25° C., for at least 1 hour.

In certain embodiments, a compound of Formula (1) is produced. In other embodiments, a compound of Formula (1) or a salt thereof is produced. In this regard, the salt may be a pharmaceutically acceptable salt.

In yet another aspect, the present invention provides a dihydrochloride salt of the compound of Formula (I)

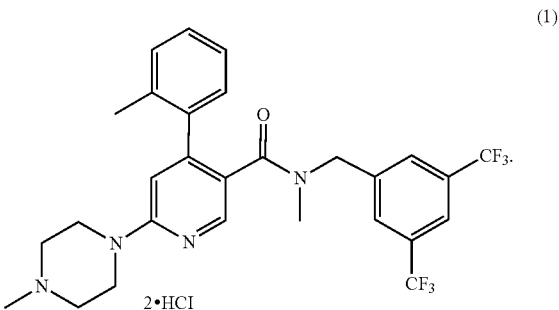 [SMILES: Cc1ccccc1-c1cc(N2CCN(C)CC2)ncc1C(=O)N(C)Cc1cc(C(F)(F)F)cc(C(F)(F)F)c1]

(1)

In particular embodiments it is desirable to produce the dihydrochloride salt substantially free of the monohydrochloride salt or trihydrochloride salt. In this regard the inventors have found that this can be achieved at an acid:base molar ratio (25° C.) of about 1.8-1.9:1, such as ratios of 1.80:1, 1.81:1, 1.82:1, 1.83:1, 1.84:1, 1.85:1, 1.86:1, 1.87:1, 1.88:1, 1.89:1, and about 1.90:1.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The following examples are intended to illustrate the invention are not to be construed as being limitations thereon.

The following reactions may be performed on a milligram, gram or kilogram scale.

Example 1

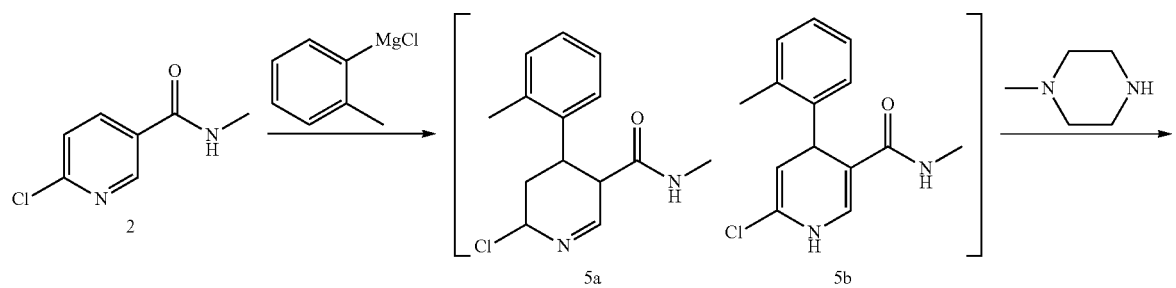

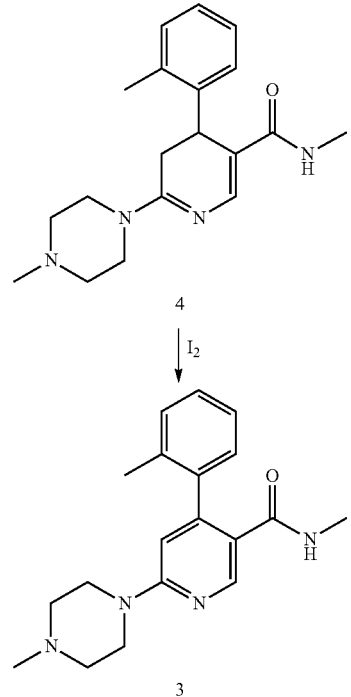

Synthesis of N-methyl-6-(4-methylpiperazin-1-yl)-4-(o-tolyl)nicotinamide (3)

1. 6-Chloro-N-methylnicotinamide is dissolved in anhydrous THF (20 vol/g) and stirred under N$_2$ at 20±5° C. (target 20° C.) for at least 3 min (colourless, slightly cloudy solution).
2. A 1 M solution of o-tolylmagnesium chloride in THF (2.5 eq) is cooled to 0±5° C. (target 0° C.) and stirred under N$_2$ (dark clear brown/black solution).
3. The 6-chloro-N-methyl nicotinamide solution is added dropwise to the o-tolyl magnesium chloride solution at 0±5° C. (target 0° C. for at least 60 min).
4. The reaction is warmed to 20±5° C. (target 20° C.) and stirred for at least 1 h (dark green/brown solution) until HPLC indicates there is ≤8% 6-chloro-N-methyl nicotinamide at 260 nm. If the HPLC specification is unable to be met, additional charges of 1 M o-tolylmagnesium chloride in THF are slowly added at 0±5° C. (target 0° C.) and stirred until the HPLC specification is met.
5. The reaction is cooled to 0±5° C. (target 5° C.) and EtOAc (6.6 g/g) is added at ≤10° C. (target 5° C.).
6. The mixture is warmed to 20±5° C. (target 20° C.) and stirred for at least 40 min.
7. N-Methylpiperazine (5 eq) is added in one portion at 20±5° C. (target 20° C.) and the reaction stirred for at least 10 h until HPLC indicates there is ≤2% Intermediate 5a at 260 nm and 330 nm.
8. The reaction mixture is cooled to 5±5° C. (target 5° C.) and 7% AcOH in water (20 vol/g) at 15±5° C. is added at such a rate that the internal temperature is maintained at ≤20° C. (approximately pH 8).
9. The layers are separated and the aqueous layer is back extracted with DCM (4×10 vol/g) (dark brown/orange/yellow solutions).
10. The combined organic layers are dried with anhydrous Na$_2$SO$_4$ (4.0 g/g), filtered and washed with DCM (2×5 vol/g).
11. The solution is concentrated under vacuum at ≤40° C. to approximately 20 mL/g of 6-chloro-N-methyl nicotinamide via solvent swaps with THF (×20 ml/g).
12. The Intermediate 2 solution is cooled to 0±5° C. (target 0° C.).
13. I$_2$ (1.5 eq) is dissolved in anhydrous THF (10 vol/g) under N$_2$ and cooled to 0±5° C. (target 0° C.).
14. The iodine solution is added dropwise to the Intermediate 2 solution at 0±5° C. (target 0° C.).
15. The reaction is warmed to 20±5° C. (target 20° C.) and stirred for at least 15 h until HPLC indicates there is ≤2% Intermediate 2 at 330 nm. If the HPLC specification is unable to be met, magnesium hydroxide (0.2 eq) and 10% v/v acetic acid in water (1.5 vol/g) are added to the reaction mixture at 0±5° C. (target 0° C.), warmed to 20±5° C. (target 20° C.) and stirred for at least a further 15 hours until the HPLC specification is met.
16. The reaction is cooled to 5±5° C. (target 5° C.) and 10% Na$_2$S$_2$O$_3$ in water (10 vol/g) is added at such a rate that the internal temperature is maintained at ≤10° C.
17. The THF is distilled under vacuum at ≤40° C.
18. The solution is cooled to 5±5° C. (target 5° C.) and 2 M HCl (approximately 3.5 vol/g) is added to adjust the pH to 1 to 2 (target pH 1.5) at ≤10° C.
19. The aqueous layer is extracted with EtOAc (3×30 vol/g).
20. The aqueous layer is cooled to 5±5° C. (target 5° C.) and 2 M NaOH (approximately 4 vol/g) is added to adjust the pH to 8 to 9 (target pH 8.5) at ≤10° C.
21. The aqueous layer is extracted with DCM (3×30 vol/g) and the combined organic layers are dried with anhydrous Na$_2$SO$_4$ (2 g/g), filtered and washed with DCM (2×5 vol/g).
22. The solution is concentrated under vacuum at ≤40° C. until the volume decreases to about 20 mL/g.

23. A solvent swap with MTBE (20 vol/g) is performed by cooling the solution to 20±5° C. (target 20° C.) and adding MTBE slowly over 20 to 40 min (target 30 min). The solution is concentrated under vacuum at ≤40° C. until the volume decreases to about 20 mL/g.
24. The solvent swap with MTBE (20 vol/g) is repeated at least twice until GC indicates the DCM content is ≤3%.
25. The resultant suspension is granulated for at least 1 hour at 20±5° C. (target 20° C.).
26. The product is filtered, washed with MTBE (5×6 mL/g) and dried under vacuum at 35±5° C. to afford an off-white to brown solid, the compound being that of Formula (3) in a yield of 64%.

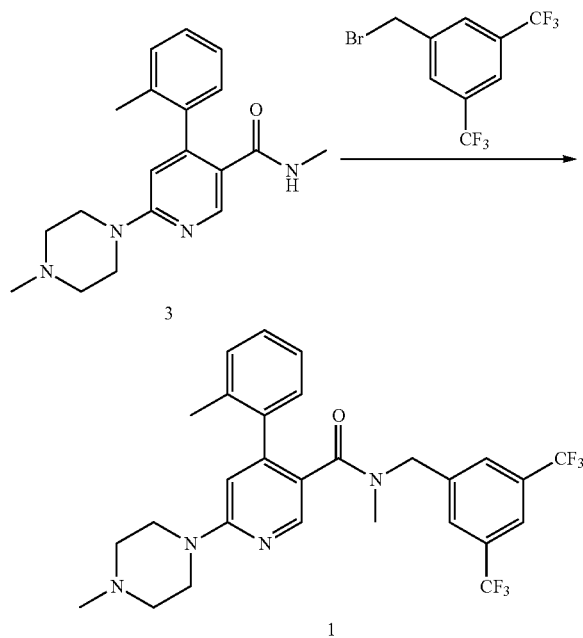

Synthesis of N-{[3,5-Bis(trifluoromethyl)phenyl]methyl}-N-methyl-4-(2-methylphenyl)-6-(4-methyl-1-piperazinyl)-3-pyridinecarboxamide (1)

1. Intermediate 3 (1 eq) is dissolved in anhydrous THF (10 vol/g) under $N_2$ at 20±5° C. (target 20° C.) and cooled to −2.5±7.5° C. (target 0° C.).
2. Potassium tert-butoxide (1.5 eq) is added at ≤5° C. and stirred for at least 15 min.
3. 3,5-Bis(trifluoromethyl)benzyl bromide (1.2 eq) is added dropwise over at least 30 min at ≤5° C.
4. The reaction mixture is stirred for at least 30 min at ≤5° C. until HPLC indicates there is ≤2% Intermediate 3 at 260 and 300 nm.
5. Upon completion of the reaction, water (10 vol/g) is added at ≤20° C.
6. The reaction mixture is acidified to pH 1 to 2 (target pH 1.5) using 2 M HCl (approximately 3 vol/g) at ≤20° C.
7. The acidified solution is washed with n-heptane (1×10 vol/g).
8. The aqueous layer is basified to pH 8 to 9 (target pH 8.5) using 2M NaOH (approximately 3 vol/g) at ≤20° C.
9. The aqueous layer is back-extracted with DCM (3×10 vol/g).
10. The combined DCM layers are dried with anhydrous $Na_2SO_4$ (2 g/g Stage IV) and circulated through a silica gel 60 plug (0.4 g/g) three times. The plug is washed with DCM (2×2 vol/g).
11. The solution is concentrated under vacuum at 40° C. until the volume decreases to about 10 mL/g.
12. The solution is cooled to 0±5° C. (target 0° C.) and 2 M HCl in ether (1.5 eq) is added dropwise at such a rate that the internal temperature is maintained at 0±5° C. (target 0° C.).
13. The beige suspension is stirred at −0±5° C. for at least 1 h.
14. A solvent swap with MTBE (20 vol/g) is performed by cooling the solution to 20±5° C. (target 20° C.) and adding MTBE slowly over 20 to 40 min (target 30 min). The solution is concentrated under vacuum at ≤40° C. until the volume decreases to about 10 mL/g.
15. The solvent swap with MTBE (20 vol/g) is repeated twice until GC indicates the DCM content is ≤3% w/w.
16. The resultant suspension is granulated for at least 1 hour at 20±5° C. (target 20° C.).
17. The product is filtered, washed with MTBE (2×2.5 mL/g) and dried under vacuum at 55±5° C. to afford an off-white to yellow solid in a yield of 75%.
18. The product is milled and dried under vacuum further at 55±5° C. to afford an off-white to yellow solid, the compound being that of Formula (1) in a yield of 95%.

Example 2—a) Initial Salt Screen Studies

The solubility of compound of Formula (1) was first qualitatively studied in 50 solvents. In all SAS experiments, the amorphous free base of compound of formula (1) was obtained after evaporation of the experiments. The free base is very soluble or soluble in almost all solvents, with water being the only antisolvent.

Salt formation has been investigated in a screen consisting of 144 experiments. The screen was designed to include the most suitable concentrations for an aqueous based intravenous formulation of the compound of formula (1). The screen employed 12 solvents, 12 acids and 1 molar ratio of 1:1.05 base to acid. Six monoprotic acids were used, together with six di or polyprotic acids. The 12 solvent systems used, spanning most solvent classes, are as follows: $H_2O$, ethanol, 2-propanol, ethyl acetate, isobutyl acetate, acetone, methyl ethyl ketone, diethyl ether, acetonitrile, heptane, cumene and DMSO.

The following 12 counter-ions were used: Formic acid; Acetic acid; Oxalic acid; Citric acid; Tartaric acid; Phosphoric acid; Hydrochloric acid, (37%, aq.); Hydrobromic acid (48%, aq.); Sulfuric acid (98%); Methanesulfonic acid; p-Toluenesulfonic acid and Ethane-1,2-disulfonic acid. Most experiments were conducted in solution, with the exception of those in water or with citric, tartaric, p-toluenesulfonic and 1,2-ethanedisulfonic acids, which were performed as slurries.

In the case of water experiments, most experiments resulted in clear solutions after ageing at RT for 72 hrs. Some experiments showed slight turbidity, however no solids could be harvested. After cooling for 24 hrs at 5° C. no solids were obtained. The experiments were finally evaporated at 60° C. and 10 mbar and the solids obtained measured.

In the case of Ethanol, 2-propanol, ethyl acetate, ethyl methyl ketone, diethyl ether, acetonitrile and heptane experiments, solids were obtained after ageing at RT. If no precipitation occurred after 72 hrs of ageing, the samples were first cooled to −20° C., and, if no solids were obtained, evaporated at 30° C. and 10 mbar.

In the case of Cumene experiments, solids were obtained after ageing at RT. If no precipitation occurred after 72 hrs of ageing, the samples were first cooled to −20° C., and, if no solids were obtained, evaporated at 90° C. and 10 mbar.

In the case of DMSO experiments, no solids were obtained after ageing at RT for 48 h. To each experiment diethyl ether was added as salt antisolvent in a 10:1 ratio (2 mL). As this did not result in any solids, the solutions were let to cool at 5° C. overnight. In most cases phase separation of a yellow viscous liquid was observed. Finally, the samples were evaporated at 30° C. and 100 mbar for 24 h, followed by 24 h at 90° C., 10 mbar in order to obtain solids.

The following results were obtained:

Formic acid experiments: no XRD patterns were observed. All the experiments resulted in amorphous materials.

Acetic acid experiments: no XRD patterns were observed. All the experiments resulted in amorphous materials.

Oxalic acid experiments: 2 patterns were obtained. Both patterns remained unchanged after stability tests. DSC analyses indicate two thermal events, probably melting followed by decomposition at higher temperatures. HPLC purity was >98%.

Citric acid experiments: 4 patterns were obtained. After stability almost all the samples transformed to a single pattern. TG and DSC analyses indicate that this form melts with decomposition, as compared to the freebase which showed no clear thermal events. HPLC purity was 100%.

Tartaric acid experiments: 2 patterns were obtained. All experiments transformed into a single pattern following the stability experiments. TG analyses shows two thermal events, melting, followed immediately by thermal decomposition. HPLC purity was 100%.

$H_3PO_4$ acid experiments: 1 pattern was obtained after stability. DSC analyses show two distinct endothermic events occurring, probably melting followed by decomposition at higher temperatures. HPLC purity was 100%.

HCl experiments: 1 pattern was obtained in three experiments. After stability, this pattern appeared in one more experiment. HPLC purity was >99%.

HBr experiments: 3 patterns were obtained and all experiments resulted in crystalline materials. Only one of them transformed in the other one during test testing. TG and DSC analyses indicate a clear melting event without mass loss. HPLC purity was >99%.

$H_2SO_4$ experiments: 1 diffraction pattern was obtained in only 1 experiment. After stress test all experiments resulted in amorphous material. DSC analysis indicates an endothermic event at higher temperatures, but was inconclusive. HPLC purity was >99%.

Methanesulfonic acid experiments: 1 pattern was obtained in the majority of experiments. This remained unchanged after stability tests, with the exception of one experiment where a new diffraction pattern was observed. DSC analysis several unassignable thermal events, as compared to the freebase which showed no clear thermal events. HP LC purity was 100%.

P-Toluenesulfonic acid experiments: 3 patterns were observed. After stability all experiments converted into crystalline materials, with a new diffraction pattern appearing. DSC analyses proved inconclusive due to small amounts of materials. HPLC purity were >97%.

1,2-Ethanedisulfonic acid experiments: 6 patterns were obtained. After the stress test most transformed into amorphous materials, with two exceptions. One of these two corresponds to a new diffraction pattern. DSC analyses show a few endothermic events which can be assigned either to polymorphic transitions or melting events. HPLC purity was >98%.

Initial conclusion—salt screen highlighted citrate, tosylate, tartrate, bromide, 1-2-ethane-disulfonic acid, hydrochloride, and mesylate as the most suitable candidates for salt formation based on the following criteria: crystallinity (heavier weighting), and polymorphic behaviours, solubility and stability.

b) Secondary Salt Screen Studies

Based on scale up ability criteria (higher yields and amounts) it was decided to further investigate the mono-HCl, citrate and tartrate salts in terms of physio-chemical characterisation, preliminary stability and aqueous solubility.

The results are summarised as follows: All three salts could be obtained in multigram and kilogram scale.

The citrate salt was obtained in the 2nd attempt from ethyl acetate solvent at 1.05:1 acid:base molar ratio and 25° C. The salt precipitated after ageing 3 days. The XRPD pattern was consistent with the "citrate 1" pattern identified during the initial salt screen. The first scale-up experiment resulted in material with low crystallinity which improved after exposure at 40° C./75% RH. A 3rd scale-up experiment performed in the same conditions as the 2nd scale-up experiment was successful in producing "citrate 1".

The tartrate salt was obtained in the first attempt from acetonitrile, at 1.05:1 acid:base molar ratio, after ageing 3 days. The pattern of the crystalline solids obtained in the first experiment corresponded to the "tartrate 2" pattern identified during the initial screen.

The mono chloride salt was obtained in the 3rd attempt from diethyl ether at 1.05:1 acid:base molar ratio, after ageing 3 days. The pattern of the crystalline solids obtained in the experiment corresponded to the "chloride 1" pattern identified during the initial screen.

First attempt resulted in a new crystal form undetected during salt screen and denotes as "chloride 2". Second attempt resulted in an amorphous material which improved in crystallinity ("chloride 1") after exposure at 40° C./75% RH.

The main properties and characteristics of the scaled-up salts are briefly presented in Table 1. "pH max" represents the pH at which the compound has the maximum solubility "Smax". Decomposition/melting range temperature and presence of solvate molecules are estimated from thermal analyses. The polymorphism risk was assessed base on the number of identified forms during this work and reproducibility of the salt screen target patterns.

TABLE 1

| Property/ analysis method | Tartrate 2 | Citrate 1 | Chloride 1 |
| --- | --- | --- | --- |
| pHmax | Within 1.8-2.3 | Within 2.9-4.3 | Undetermined |
| Smax (mg/mL) | More than 8.4 | More than 109 | Undetermined |
| Melting range/ Decomposition (° C.) | 178 | 156 | 120-124 |
| Solvate present | No | No | Potential hydrate ("chloride 2") |

TABLE 1-continued

| Property/analysis method | Tartrate 2 | Citrate 1 | Chloride 1 |
|---|---|---|---|
| Hydroscopicity (Water sorption at 90% RH) | 1.9% | 1.0% | 3.2% |
| Stability-Light, 80° C., 400° C./75% RH | Stable | Stable | Stable |
| Oxidative stress behaviour (H2O2 3%) | Stable | Degradation (on HPLC) | New form (by XRPD) |
| Aqueous unbuffered solubility (mg/mL) | 1.61 (pH = 2.8) | 16.12 (pH = 2.72) | 8.32 (pH = 3.00) |

TABLE 1-continued

| Property/analysis method | Tartrate 2 | Citrate 1 | Chloride 1 |
|---|---|---|---|
| NMR analysis | Salt likely | Salt likely | Salt likely |
| Polymorphism risk | Medium | Medium | High |

Conclusions on Secondary Screen—

Regarding crystallinity—this could be achieved by precipitation. The choice of solvents seems to be very important as in the case of citrate and chloride when precipitation did not occur by ageing of experiments, fast evaporation of the solutions yielded amorphous solids. The mono chloride likely forms hydrates or polymorphs and tartrate has probably a new form as recorded by XRPD in some of the disproportionation studies. All 3 salts present good thermal stability as well as solid state stability up to 1 week in the presence of ambient light, elevated temperatures and humidity. Citrate suffered degradation (as concluded by HPLC) in peroxide hydrogen 3%.

As a general conclusion, all salts present both good properties and drawbacks. From the set of 3 scaled-up salts, citrate and chloride are the most promising. The main drawback of monochloride is the probability to form hydrates, while the citrate presented degradation in oxidative conditions and disproportionation at pH 4.5 which did not occur in the case of chloride.

It was then contemplated to proceed with trying to see if one could produce the di and tri-hydrochloride salt of compound of formula (1) and investigate the suitability of these new salt forms.

Example 3—Production of 2HCl Salts of Compound of Formula (1)

About 2 M (1.8-1.9 M) hydrogen chloride in diethyl ether solution is slowly charged to the solution containing the free base of Compound of Formula (1). The mixture is stirred then warmed and tert-butyl methyl ether is charged slowly. The mixture is concentrated under a slight reduced pressure to an approximate volume of 0.01 L/g of Compound of Formula (1) and then cooled. The solvent swap process with tert-butyl methyl ether is repeated until GC indicates the dichloromethane content is s 3% w/w. The resultant suspension is granulated, isolated by filtration and each wet cake washed with tert-butyl methyl ether. The 2HCl salt is dried in a vacuum oven to constant weight to afford an off-white to yellow solid. The solid is then milled and dried further to yield the final 2HCl salt drug substance.

TABLE 2

Summary of Changes to Drug Substance Batches used in the Regulatory Development of 2HCl salt of Compound of Formula (1).

| Batch | Change |
|---|---|
| 117606 | Not applicable |
| 117621 | This batch was prepared from the filtrate of batch 117606 by combining with a portion of the first crop of 11706, resuspending in tert-butyl methyl ether, filtering and drying. |
| 117771 | The synthesis of batch 117606 included a slight excess of 2M hydrogen chloride in diethyl ether solution, which results in the synthesis of the trihydrochloride salt. The batch was subsequently converted to the free base and the dihydrochloride salt was prepared. For batch 117771 a smaller quantity of about 2M hydrogen chloride in diethyl ether solution was used, resulting in production of the dihydrochloride salt and removing the need for the additional step. |

Characterisation of 2HCl Salt of Compound of Formula (1)

Elemental analysis was performed on reference standard 117621, with results as follows:

Found: C, 53.85%; H, 5.11%; Cl, 11.27%; N, 9.03%

Requires: C, 53.94%; H, 4.85%; Cl, 11.37%; N, 8.99%

The data for batch 117621 are consistent with those theoretically expected for 2HCl salt of Compound of Formula (1).

FT-IR—2HCl salt of Compound of Formula (1)—see FIG. 1.

Figure 2:
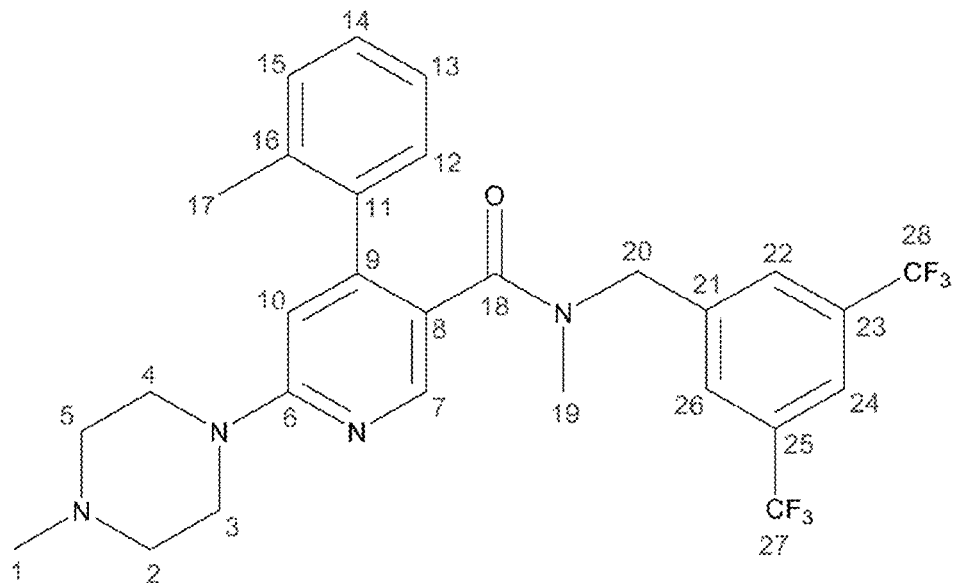
FIG. 2—$^1$H-NMR Spectrum of Compound (1) Free Base (400 MHz, DMSO-d6) (20.5 mg) (Relative to DMSO-$d_6$ at 2.50 ppm).
Figure 4:
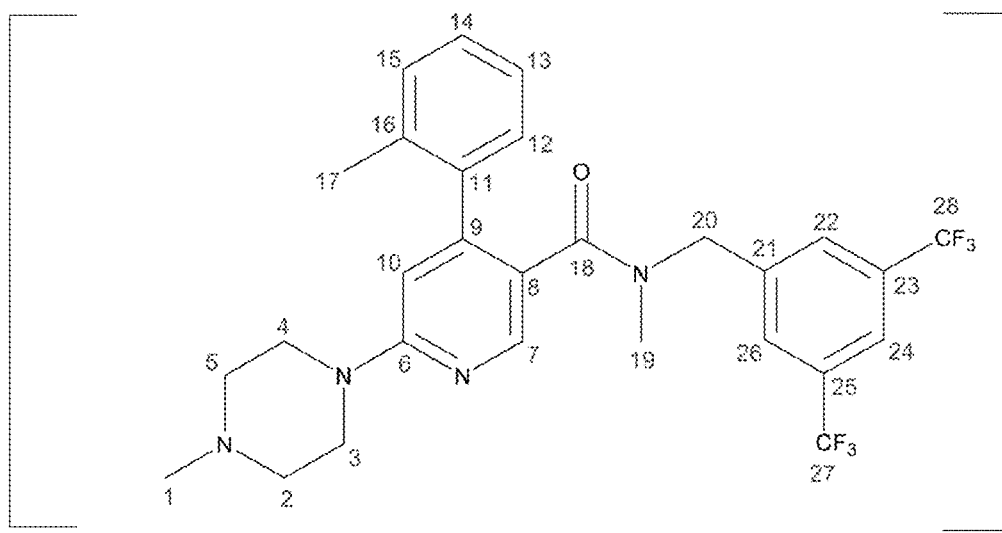

Mass Spectroscopy—Mass spectroscopy was performed on reference standard 117621, with data presented in FIG. 2. X-Ray Powder Diffraction (XRPD) and Differential Scanning Calorimetry (DSC)

Figure 7:
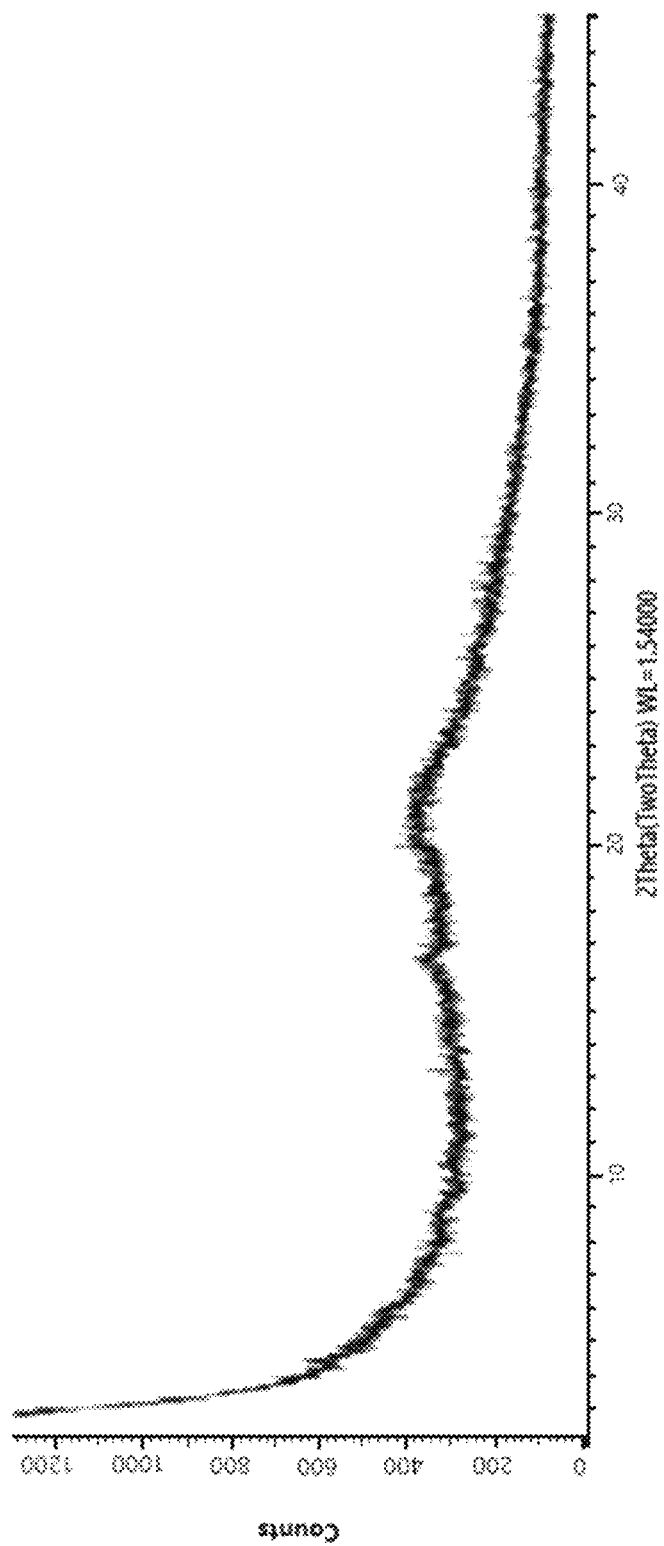
FIG. 7—XRPD of Compound (1) 2HCl salt.
Figure 8:
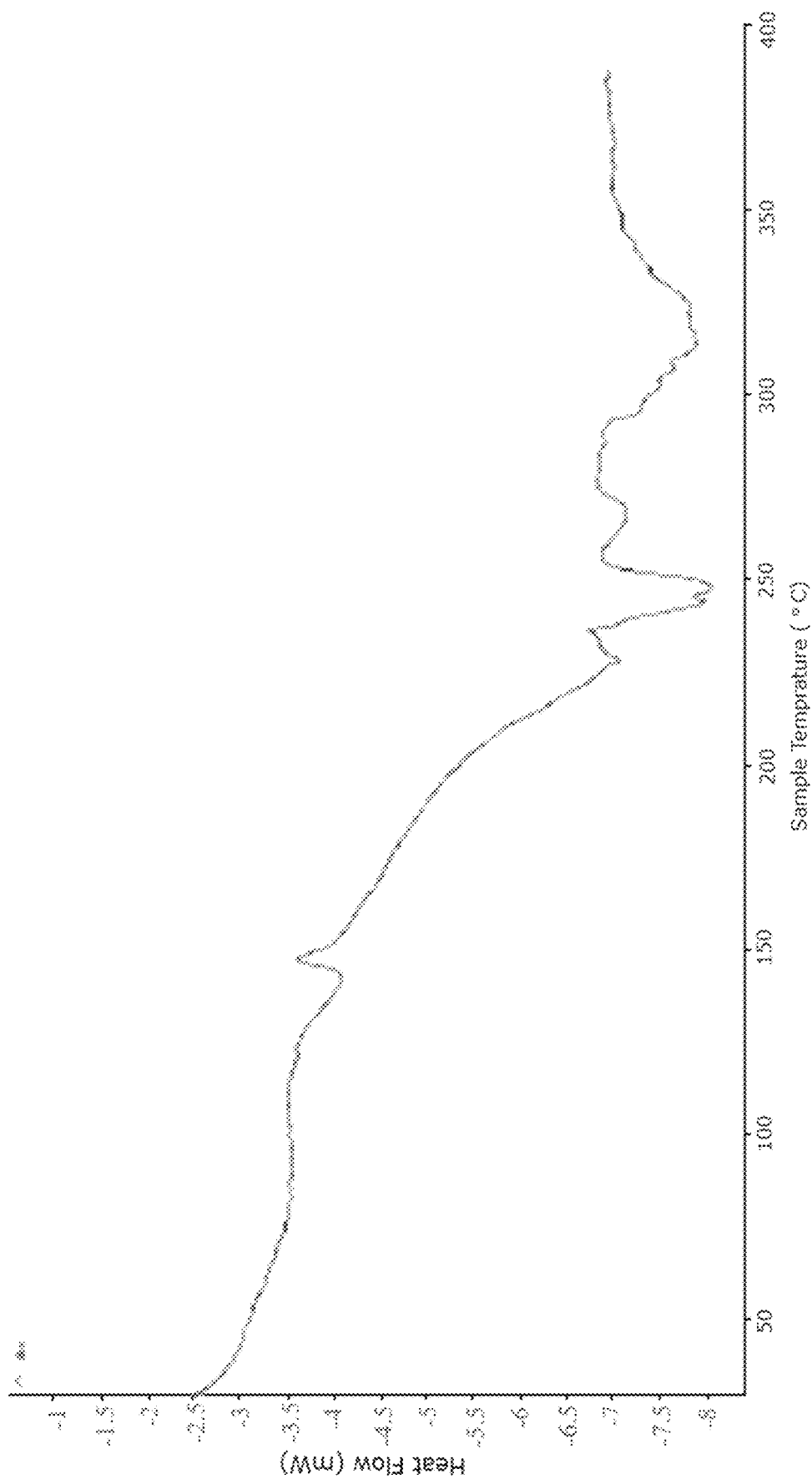
FIG. 8—DSC of Compound (1) 2HCl salt.

The XRPD and DSC analyses indicate that compound of Formula (1) 2HCl is amorphous (see FIGS. 7 and 8).

Physicochemical Characteristics

A summary of the physicochemical characteristics of 2HCl salt of Compound of Formula (1) is provided below.

Appearance: white to yellow powder

Solubility: very soluble in water (<0.2 mg/µL), freely soluble in ethanol (0.1-0.2 mg/µL), sparingly soluble in 1-propanol and acetonitrile (0.01-0.03 mg/µL).

Melting range: 120-124° C.

pKa (free base): estimate pKa 1=7.54, pKa 2=4.05; calculated pKa 1=7.07

Hydroscopicity (water sorption at 90% RH): 3.2% pH: 2 to 3 (5 mg/mL solution in purified water).

Polymorphism: Not detectable.

Stability Data

TABLE 3

| | | Compound of formula (1) 2HCl salt - Samples Stored at 40° C./75% RH | | | | |
| --- | --- | --- | --- | --- | --- | --- |
| | Acceptance | | Time Point ((mon(months)) | | | |
| Parameter | Criteria | Initial Release | 0 | 1 | 3 | 6 |
| Date Due | | Manufacturing | 23 Dec. 2016 | 23 Jan. 2017 | 23 Mar. 2017 | 23 Jun. 2017 |
| Date Tested | | date: 16 Sep. 2016 | 23 Dec. 2016 | 24 Jan. 2017 | 23 Mar. 2017 | 3 Jul. 2017 |
| Appearance | White to yellow powder | Complies | Complies | Complies | Complies | Complies |
| pH | Report result | 2.31 | 2.31 | 2.39 | 2.33 | 2.47 |
| Water Content | Report result (%) | 1.0% | 5.0% | 4.99% | 5.58% | 5.17% |
| Assay | Report result (% "as is") | 98.3% | 95.0% | 94.8% | 94.5% | 94.6% |
| | Report result (% anhydrous) | 99.3% | 100.0% | 99.8% | 100.1% | 99.7% |
| Related Substances | Intermediate 3: NMT 1.0% RRT - 0.89: NMT 0.5% RRT - 1.27: NMT 0.5% | Int 3: 0.71% RRT 0.87: 0.35% RRT 1.27: 0.28% | Int 3: 0.69% RRT 0.85: 0.34% RRT 1.27: 0.27% | Int 3: 0.71% RRT 0.89: 0.36% RRT 1.28: 0.27% | Int 3: 0.71% RRT 0.90: 0.36% RRT 1.27: 0.26 | Int 3: 0.71% RRT 0.90: 0.35% RRT 1.27: 0.27% |
| | Any other unknown: NMT 0.2% | | RRT 0.89: 0.007% | RRT 0.90: 0.07% | RRT 0.91: 0.05% | RRT 0.91: 0.06% |
| | Total Impurities: NMT 2.0% | 1.34% | 1.37% | 1.41% | 1.38% | 1.39% |
| Microbial Limits | | | | | | |
| Total Aerobic Microbial Count | NMT 1000 cfu/g | 50 cfu/g | 50 cfu/g | NR | NR | NR |
| Total Combined Yeast and Mold Count | NMT 100 cfu/g | <100 cfu/g | <100 cfu/g | NR | NR | NR |
| *Escherichia Coli* | Absent in 1 g | Absent | Absent | | | |
| Bacterial Endotoxins | NMT 3.3 EU/mg | <0.012 EU/mg | <0.012 EU/mg | NR | NR | NR |

ND = Not detected,
NR = Not required

What is claimed is:

1. A method of preparing multi-kilogram scale amounts of a dihydrochloride salt of the compound of Formula (1) under GMP conditions,

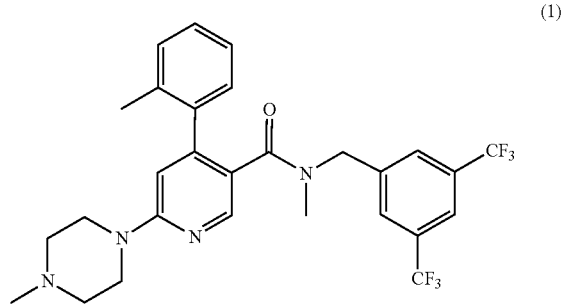 [SMILES: Cc1ccccc1-c1cc(N2CCN(C)CC2)ncc1C(=O)N(C)Cc1cc(C(F)(F)F)cc(C(F)(F)F)c1]

(1)

the method comprising:
a) treating a compound of Formula (2):

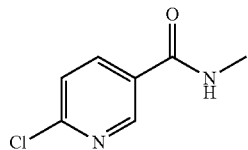

(2)

sequentially with o-tolylmagnesium chloride, N-methylpiperazine and iodine, under conditions sufficient to obtain a compound of Formula (3):

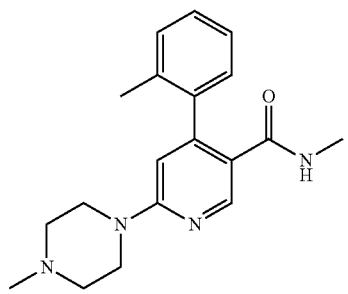

(3)

b) treating the compound of Formula (3) from step a) with 3,5-bis(trifluoromethyl)benzyl bromide and a suitable base, under conditions sufficient to obtain a compound of Formula (1);
wherein the iodine is reacted as a THF solution at about 0° C.; and
wherein the suitable base in step b) is potassium tert-butoxide and wherein the compound of Formula (3) from step a) is purified by a solvent swap with methyl tert-butyl ether (MTBE) prior to a subsequent reaction, and subsequently,
c) treating the compound of Formula (1) with a solution of hydrochloric acid in diethyl ether, under conditions sufficient to obtain a dihydrochloride salt of the compound of Formula (1), and wherein the compound of Formula (I) is not isolated prior to conversion of the compound of Formula (1) to a salt, and wherein the compound of Formula (1) from step b) is purified by a solvent swap with methyl tert-butyl ether (MTBE) prior to a subsequent reaction to form the dihydrochloride salt.

2. The method according to claim 1, wherein step (a) is conducted in THF.

3. The method according to claim 2, wherein Formula (2) is added to 1 M o-tolylmagnesium chloride in THF at about 0° C.

4. The method according to claim 1, wherein N-methylpiperazine is added at about 20° C.

5. The method according to claim 1, wherein about 5 M equivalents of N-methylpiperazine relative to the compound of Formula (2) is added to form a reaction mixture.

6. The method according to claim 1, wherein the reaction mixture is cooled after step a) to form a cooled reaction mixture, and the cooled reaction mixture is stirred for at least 10 hours at about 20° C.

7. The method according to claim 6, wherein to the cooled reaction mixture is added AcOH.

8. The method according to claim 1, wherein 3,5-Bis(trifluoromethyl)benzyl bromide is reacted with Formula (3) at about 1.2 mol equivalent.

9. The method according to claim 1, wherein the compound of Formula (2) is added to 1 M o-tolylmagnesium chloride in THF at about 0° C., over about 1 hr.

10. The method according to claim 9, wherein the reaction is warmed to about 20° C.

11. The method according to claim 5, wherein about 5 M equivalents of N-methylpiperazine relative to the compound of Formula (2) is added in one portion to form the reaction mixture.

12. The method according to claim 6, wherein the reaction mixture is cooled to about 5° C. to form the cooled reaction mixture, and the cooled reaction mixture is stirred for at least 10 hours at about 20° C.

13. The method according to claim 7, wherein to the cooled reaction mixture is added AcOH, which is about 7% AcOH in water.

14. The method according to claim 1, wherein the iodine is subsequently reacted as a THF solution, at about 1.5 mol equivalents relative to the compound of Formula (2), under nitrogen at about 0° C.

15. The method according to claim 1, wherein the base of step b) is potassium tert-butoxide, in an amount of about 1.5 mol equivalents relative to the compound of Formula (3).

16. The method according to claim 1, wherein the step c) of treating the compound of Formula (1) with a solution of hydrochloric acid in diethyl ether involves using an acid:base molar ratio (25° C.) of about 1.80, 1.81, 1.82, 1.83, 1.84, 1.85, 1.86, 1.87, 1.88, 1.89, or 1.90.

* * * * *